United States Patent [19]

Patch

[11] Patent Number: 4,482,319
[45] Date of Patent: Nov. 13, 1984

[54] MATRIX BAND INSET

[75] Inventor: Stanley J. Patch, Great Lakes, Ill.

[73] Assignee: The United States of America as represented by the Secretary of the Navy, Washington, D.C.

[21] Appl. No.: 487,666

[22] Filed: Apr. 22, 1983

[51] Int. Cl.³ .............................................. A61C 5/04
[52] U.S. Cl. .................................... 433/39; 24/23 B; 24/200
[58] Field of Search ................... 433/39, 23, 155, 149; 24/23 B, 198, 200

[56] References Cited

U.S. PATENT DOCUMENTS

| 376,548 | 1/1888 | Reed | 433/39 |
|---|---|---|---|
| 980,529 | 1/1911 | Ivory | 433/39 |
| 2,035,135 | 3/1936 | Lebow | 433/39 |
| 2,529,174 | 11/1950 | Muller | 433/155 |
| 3,854,210 | 12/1974 | Franklin et al. | 433/39 |
| 4,024,643 | 5/1977 | Eisenberg | 433/39 |

FOREIGN PATENT DOCUMENTS

| 546622 | 11/1922 | France | 24/23 B |
|---|---|---|---|
| 570492 | 7/1945 | United Kingdom | 24/23 B |

Primary Examiner—John J. Wilson
Attorney, Agent, or Firm—Robert F. Beers; Frederick A. Wein

[57] ABSTRACT

A dental inset for cooperative retainment about a tooth of an external matrix band by a retainer is presented. The matrix band is provided with oppositely disposed end portions and the inset connects the end portions of the matrix band where the end portions divaricate from the tooth so that a 360 degree matrix which readily adapts to the cervical circumference of the molar teeth is provided.

1 Claim, 4 Drawing Figures

MATRIX BAND INSET

BACKGROUND

The present invention relates to dental impliments, and more particularly, to a matrix band inset which can be used in combination with a Tofflemire matrix band retainer or the like for providing a close contour conforming circumferential matrix for the cervical circumference of molar teeth and the like.

Commonly used matrix band retainers create a triangular void in the area where the band ends enter the retainer. Although the Tofflemire matrix band retainer has advantage of adaptability, low cost, and availability, it also has this commonly associated disadvantage of the triangular shaped void being created. In cases where minimum tooth structure remains, or where there are large carious lesions in the molar teeth, there is great difficulty with current retainers for forming a well adapted, firm matrix which can securely grasp the remaining tooth structure. Additionally, the triangular shaped void further reduces the retentiveness of the matrix to the tooth.

To overcome this difficulty, dentists have improvised a variety of personal techniques. Custom fit pieces of stainless steel can be wedged into the created matrix band void. Copper bands can be adapted to the tooth, as can "T" bands or an AUTOMATRIX TM can be used. As an alternative, amalgam can simply be forced into the void and later carved to contour. All of these improvised techniques have limitations in that they can injure the gingiva and they do not contribute to matrix retention. Additionally, the improvised techniques are not adjustable and make formation of well formed proximal contacts difficult.

A further difficulty often encountered with present matrix techniques is the difficulty of attempting to adapt the matrix band to concave areas of a tooth. This is especially critical when only minimum tooth structure is remaining such as for molars which have suffered extensive tooth structure loss due to decay and for molars which have suffered cusp fracture extending subgingivally.

Accordingly, it is desirable to provide a matrix band inset for use with a matrix band retainer which provides a matrix closely contour conforming to the cervical circumference of a tooth and especially, molar teeth. It is further desirable to provide a matrix band inset which permits a firm grasp of severely damaged teeth. It is also desirable to provide a matrix band inset which allows repetative adjustment of the matrix band for enabling formation of well formed proximal contacts. It is also desirable to provide a matrix band inset permitting adaptation to concave areas of a severely damaged tooth.

SUMMARY OF THE INVENTION

Briefly, the present invention relates to a dental inset for cooperative retainment about a tooth of an external matrix band by a retainer. The matrix band is provided with oppositely disposed end portions and the inset comprises means for connecting the end portions of the matrix band where the end portions divaricate from the tooth so that a 360 degree matrix which readily adapts to the cervical circumference of the molar teeth is provided.

Accordingly, it is an object of the present invention to provide a means in combination with a matrix band and matrix band retainer for providing a 360 degree close contour conforming matrix for the cervical circumference of teeth, and in particular, molar teeth. It is another object of the present invention to provide a dental inset which is contour conformable to an abuttingly engagable portion of a tooth. It is a further object of the present invention to provide a dental inset having a prefabricated shaped portion fittable into a complementary shaped portion of a tooth.

Further objects and advantages of the present invention will become apparent as the following description proceeds and features of novelty characterizing the invention will be pointed out with particularity in the claims annexed to and forming a part of this specification.

DESCRIPTION OF THE DRAWINGS

For a better understanding of the present invention reference may be had to the accompanying drawings wherein.

DETAILED DESCRIPTION OF THE PREFERRED EMBODIMENT

Figure 1:
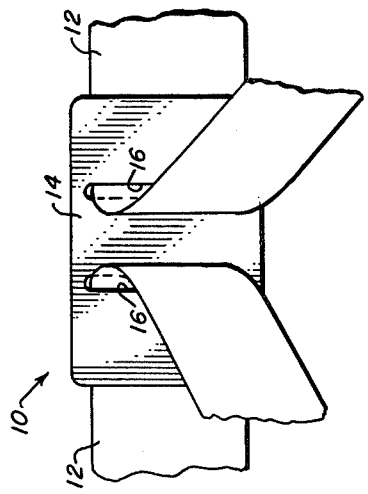
FIG. 1 is an isometric plan view of the inset of the present invention installed onto a matrix band.

Referring now to the drawings wherein like reference numerals have been applied to like members there is shown in FIG. 1 a dental inset, generally designated 10, mounted to a matrix band 12, which in turn, along with inset 10, can be mounted onto a tooth (not shown) by a matrix band retainer (not shown), typically a Tofflemire retainer.

The inset 10 when used in combination with matrix band 12 held about a tooth by a matrix band retainer, permits a 360 degree matrix which adapts readily to the cervical circumference of molar teeth. The user of inset 10 eliminates the wedge-shaped void created where the ends of the matrix band divaricate from the tooth to enter the retainer.

More particularly, the inset 10 comprises a generally planar plate 14 formed by appropriate means, e.g. stamping, from an autoclavable stainless steel with a thickness, in the examplary embodiment, of between three thousandths to five thousandths of an inch. This range of thickness permits inset 10 to be generally flexible and conform to the shape of the tooth. A thickness of 0.005 inches will still have some flexibility and a thickness of 0.003 inches will have greater contour conforming characteristics with sufficient rigidity to maintain the matrix band in proper position.

Figure 2:
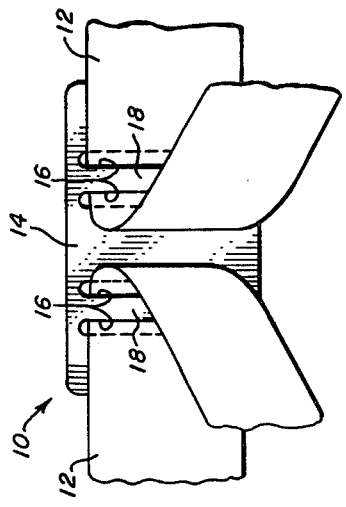
FIG. 2 is an isometric plan view of another embodiment of the dental inset of FIG. 1.

Plate 14 is provided with at least one pair of spaced apart apertures 16 (FIG. 1) extending through the thickness of plate 14 and which in the examplary embodiment are elongated. Shown in FIG. 2 is an alternate embodiment wherein there is shown two pairs of spaced apart apertures 16 with each pair of apertures forming a strap portion 18. The matrix band 12 can be threaded through apertures 16 as shown in FIGS. 1 and 2.

The elongated apertures 16 can be parallel to each other, as shown in FIGS. 1 and 2, or in an alternate embodiment, can be oblique to each other and converge toward an occlusal edge 18. In the exemplary embodiments, divergences of 15° to 35° from an imaginary altitude centerline 22 as indicated by the angles α can be used. More oblique tooth shapes would more readily accept thinner band insets and the aperture divergence will tend to correspond to the desired angulation and convexity of the amalgam restoration.

Figure 3:
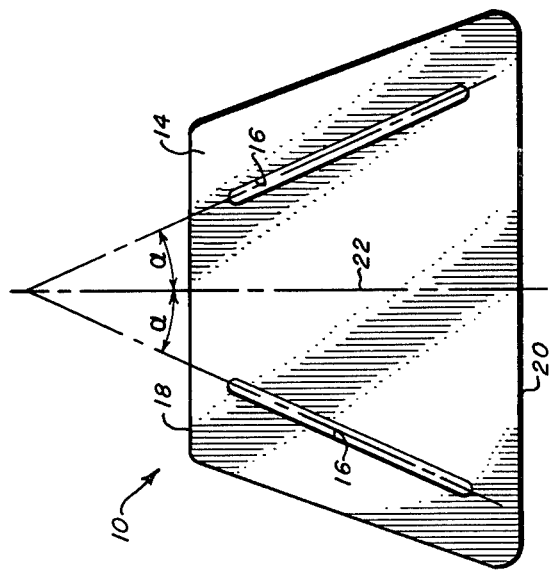
FIG. 3 is an isometric plan view of the dental inset of FIG. 1 showing one embodiment of apertures therein.

In the exemplary embodiment as shown in FIG. 3, the occlusal edge 18 is 5.0 millimeter, a gingival edge 20 can be 7.0 to 10.5 millimeters, the total height along centerline 22 can be 8.0 millimeter, and the length of the apertures 16 can be approximately 6.5 millimeters as projected onto centerline 22.

Figure 4:
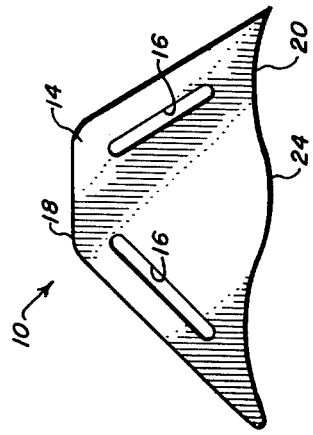
FIG. 4 is an isometric oblique view of the dental inset of FIG. 3 showing a prefabricated shaped portion.

Referring now to FIG. 4 there is shown inset 10 having a prefabricated shaped portion 24 which is a cervical area of the inset contoured to adapt to the buccal cervical concavity above the furcation area of a lower molar, or the lingual, or mesial surfaces of many teeth. In such a case, the convex side of the dent should be oriented at the cervical extent of the matrix and directed towards the tooth. Additionally, an appropriate inset can be placed to engage the undercut produced by the concave area directly cervical to a root bifurcation. Thus, two insets can be used simultaneously to engage both the buccal and lingual cervical concavities of a lower mollar. Having oriented the insets, the matrix band can be threaded through the apertures in the inset and thence into the matrix band retainer, such as a Tofflemire retainer. The matrix band ends can then be secured by the retainer as usual. If necessary, gingival tissue could be removed to gain access to the remaining tooth structure. The matrix band should be tightened, wedged, and burnished to contour if appropriate.

Thus, once adapted with inset 10, the matrix band can be tightened as necessary by the use of a Tofflemire retainer thus gripping the tooth firmly around the entire cervical circumference without the triangular void common with such retainers. Additionally, with inset 10, molars with the entire buccal or lingual surfaces missing can be reconstructed with a one-half or three-quarter amalgum crown and molars with decay which extends to any furcation area can be reconstructed.

Accordingly, there is presented a matrix band inset which in combination with a matrix band retainer provides a generally complete circumferential matrix for the cervical circumference of molar teeth. The inset is contour conformable to the shape of the tooth and can additionally be provided with a prefabricated shaped portion for generally fitting with engagable portions of a tooth for providing a superior matrix fit.

While there has been illustrated and described what is at present considered to be a preferred embodiment of the present invention, it will be appreciated that numerous changes and modifications are likely to occur to those skilled in the art and it is intended in the appended claims to cover all those changes and modifications which fall within the true spirit and scope of the present invention.

What is claimed is:

1. A dental inset for cooperative retainment about a tooth of an external matrix band having oppositely disposed end portions and comprising:
   a generally planar member having wall thickness, the planar member being generally flexible about the thickness and contour conformable to an abuttingly engagable portion of the tooth,
   a prefabricated shaped portion provided on the planar member generally fittable with engagable portions of the tooth and comprising a protrusion fittable into a complementary depression in the tooth, and
   means for restraining the end portions of the matrix band.

* * * * *